US010213562B2

(12) United States Patent
Thorley et al.

(10) Patent No.: US 10,213,562 B2
(45) Date of Patent: *Feb. 26, 2019

(54) VACCINATION SYRINGE

(71) Applicant: UNL Holdings LLC, New York, NY (US)

(72) Inventors: Craig Stephen Thorley, Largs (AU); Joseph Hermes Kaal, Raworth (AU); Christopher Charles Rafferty, Raworth (AU); Ian Johnson, Pennant Hills (AU); Eric Siu, Strathfield (AU); Andrew Reade, Castle Hill (AU)

(73) Assignee: UNL Holdings LLC, New York, NY (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/053,871

(22) Filed: Feb. 25, 2016

(65) Prior Publication Data
US 2016/0175541 A1    Jun. 23, 2016

Related U.S. Application Data

(63) Continuation of application No. 13/508,944, filed as application No. PCT/AU2010/001505 on Nov. 11, 2010, now Pat. No. 9,302,056.
(Continued)

(51) Int. Cl.
*A61M 5/34* (2006.01)
*A61M 5/32* (2006.01)
*A61M 5/50* (2006.01)

(52) U.S. Cl.
CPC .......... *A61M 5/3234* (2013.01); *A61M 5/502* (2013.01); *A61M 2005/3231* (2013.01);
(Continued)

(58) Field of Classification Search
CPC .... A61M 5/322; A61M 5/3234; A61M 5/502; A61M 5/508; A61M 2005/323; A61M 2005/3231; A61M 2005/5033
See application file for complete search history.

(56) References Cited

U.S. PATENT DOCUMENTS 4,944,723 A    7/1990 Haber et al.
4,994,034 A    2/1991 Botich et al.
(Continued)

FOREIGN PATENT DOCUMENTS

JP    2004-49668 A    2/2004
JP    2008-518693 A    6/2008
(Continued)

OTHER PUBLICATIONS

Australian Patent Office, International Search Report in International Patent Application No. PCT/AU2010/00155 dated Jan. 18, 2011).
(Continued)

*Primary Examiner* — Laura A Bouchelle
(74) *Attorney, Agent, or Firm* — Hamilton, Brook, Smith & Reynolds, P.C.

(57) ABSTRACT

A replaceable needle assembly is provided for a retractable, prefilled syringe comprising a barrel having a mounting member and a plunger, whereby the retractable needle can be replaced by a user without affecting the retraction mechanism. The replaceable needle assembly comprises a needle fitted to a retractable needle mount and a needle retainer. The needle mount is removably, screw-threadedly mountable to the mounting member of the barrel. The needle retainer comprises a plurality of fingers that releasably engage the retractable needle to thereby prevent inadvertent retraction of the retractable needle before engagement by the plunger. The plunger comprises a plunger seal comprising an outer member and an inner member that engages the needle for
(Continued)

spring-driven retraction. At the end of retraction, a lock is formed between the plunger and barrel to prevent re-use of the syringe.

20 Claims, 7 Drawing Sheets

Related U.S. Application Data

(60) Provisional application No. 61/260,252, filed on Nov. 11, 2009.

(52) U.S. Cl.
CPC ............... *A61M 2005/3241* (2013.01); *A61M 2005/5033* (2013.01); *A61M 2202/30* (2013.01); *Y10T 29/49826* (2015.01)

(56) References Cited

U.S. PATENT DOCUMENTS

| | | |
|---|---|---|
| 5,030,208 A | 7/1991 | Novacek et al. |
| 5,222,944 A | 6/1993 | Harris |
| 5,395,337 A | 3/1995 | Clemens et al. |
| 5,401,249 A | 3/1995 | Shields |
| 5,453,093 A | 9/1995 | Haining |
| 5,501,670 A | 3/1996 | Sak |
| 5,531,694 A | 7/1996 | Clemens et al. |
| 5,792,107 A | 8/1998 | Petrocelli |
| 6,436,076 B1 | 8/2002 | Hsu |
| 6,494,866 B1 | 12/2002 | Robinson |
| 8,167,837 B2 | 5/2012 | Judd et al. |
| 9,302,056 B2 * | 4/2016 | Thorley ............... A61M 5/3234 |
| 2003/0004468 A1 | 1/2003 | Righi et al. |
| 2004/0267209 A1 | 12/2004 | Kunishige |
| 2006/0253074 A1 | 11/2006 | Thayer |
| 2009/0093759 A1 | 4/2009 | Judd et al. |
| 2009/0118677 A1 | 5/2009 | Walton et al. |
| 2009/0240210 A1 | 9/2009 | Walton et al. |
| 2013/0338602 A1 | 12/2013 | Thorley et al. |

FOREIGN PATENT DOCUMENTS

| | | |
|---|---|---|
| JP | 2008-535589 A | 9/2008 |
| WO | WO 95/27524 A1 | 10/1995 |
| WO | WO 2006/020953 A1 | 2/2006 |
| WO | WO 2006/047810 A1 | 5/2006 |
| WO | WO 2006/108243 A2 | 10/2006 |
| WO | WO 2006/119570 A1 | 11/2006 |
| WO | WO 2007/028189 A1 | 3/2007 |
| WO | WO 2008/136775 A2 | 11/2008 |
| WO | WO 2009/003234 A1 | 1/2009 |

OTHER PUBLICATIONS

European Patent Office, European Search Report in European Patent Application No. 10829352.3 (dated Sep. 5, 2013).

U.S. Appl. No. 13/508,944, filed Nov. 12, 2012.

* cited by examiner

VACCINATION SYRINGE

CROSS-REFERENCE TO RELATED APPLICATIONS

This patent application is a continuation of U.S. application Ser. No. 13/508,944 filed May 9, 2012, which is the U.S. national stage of International Patent Application No. PCT/AU2010/001505, filed Nov. 11, 2010, which claims the benefit of U.S. Provisional Patent Application No. 61/260,252, filed Nov. 11, 2009, the disclosures of which are herein incorporated by reference.

FIELD

THIS INVENTION relates to syringes. More particularly, this invention relates to a retractable syringe that includes a replaceable, retractable needle.

BACKGROUND

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers. Further problems arise for health professionals administering medicines and vaccines to infected individuals, where accidental needle stick injury by a used syringe can lead to infection.

In response to this problem, syringes have been developed which either provide a needle sheathing mechanism or a needle retraction mechanism to prevent re-use and/or needle stick injury.

However, many such retractable syringes have fixed needles or highly specialized retractable needle assemblies that are not amenable to replacing needles which have been bent or burred or for allowing a user to select an appropriate needle size.

SUMMARY

The invention is therefore, at least in part, broadly directed to a replaceable needle assembly for a retractable syringe, whereby a retractable needle can be replaced by a user without affecting the retraction mechanism.

The invention is also broadly directed to a barrel suitable for mounting the replaceable needle assembly.

The invention also broadly provides an improved retraction mechanism comprising respective elements of the retractable needle assembly and/or a plunger capable of engaging and retracting a retractable needle.

In a first aspect, the invention provides a replaceable needle assembly for a retractable syringe comprising a plunger and a barrel having a mounting member, said replaceable needle assembly comprising: a retractable needle that is engageable by said plunger; a needle mount that is removably mountable to the mounting member of the barrel; and a needle retainer.

In one embodiment the needle mount comprises a male member which is receivable by a female member of said mounting member.

Preferably, the needle mount comprises a screw-thread which in use is received by a complementary screw thread of said mounting member.

In a preferred embodiment, the needle retainer comprises a plurality of fingers that engage said retractable needle to prevent inadvertent retraction of said retractable needle.

In a second aspect, the invention provides a barrel for a retractable syringe, said barrel comprising a mounting member to which is removably mountable a replaceable needle assembly.

In one embodiment, said mounting member comprises a female member that receives a male member of a needle mount of said retractable, replaceable needle assembly.

Preferably, the mounting member comprises a screw-thread which in use receives a complementary screw thread of a needle mount of said replaceable needle assembly.

Preferably, the barrel further comprises a needle seal coupled to the mounting member.

Preferably, the barrel comprises a releasing member.

In one embodiment, the barrel further comprises a collar.

Preferably, the collar comprises the releasing member.

In a third aspect, the invention provides a plunger for a retractable syringe comprising a retractable needle, said plunger comprising: a biasing means; a plunger member releasably connected to a control rod; a plunger housing; and a plunger seal mounted to the plunger member; wherein the plunger member, control rod and plunger housing co-operate to maintain said biasing means in an initially energized state prior to retraction.

Suitably, the plunger comprises a needle-engaging portion that is capable of engaging the retractable needle to facilitate retraction of the retractable needle.

In one embodiment, the plunger seal comprises an inner member and an outer member. Preferably, the plunger seal comprises a stop to prevent or minimize forward travel of the inner member relative to the outer member. Suitably, according to this embodiment the inner member comprises the needle-engaging portion.

Preferably, said plunger is arranged so that at the end of depression of said plunger to deliver fluid contents of said retractable syringe, said control rod disengages from said plunger housing to facilitate a release of energy from said biasing means to thereby retract said control rod and said plunger member with a needle coupled thereto.

Preferably, said needle is coupled to said inner member of said seal. An advantage of this embodiment is that because the outer member of the seal remains stationary during retraction, the "glide force" required to retract the inner member and coupled needle is relatively reduced.

Suitably, said biasing member is any device which can store energy in a releasable form, such as a spring, elastic or the like.

Preferably, said biasing means is a spring.

In a fourth aspect, the invention provides a retractable syringe kit comprising the barrel of the second aspect prefilled with fluid contents and the plunger of the third aspect in combination; and a plurality of needle assemblies according to the first aspect.

In one embodiment of the retractable syringe kit, the plurality of needle assemblies respectively comprise a 0.5 inch needle, a 1.0 inch needle and a 1.5 inch needle.

In a fifth aspect, the invention provides a retractable syringe comprising: the replaceable needle assembly of the first aspect removably mounted to the barrel of the second aspect; and/or the plunger of the third aspect.

In one embodiment, the retractable syringe further comprises a lock formed between said plunger housing and said collar of said barrel which prevents or hinders removal of the plunger housing from the retractable syringe after retraction of the retractable needle.

Preferably, the retractable syringe is a prefilled retractable syringe.

In a sixth aspect, the invention provides a method of operating a retractable syringe including the step of removably mounting a replaceable needle assembly to a barrel of a retractable syringe prefilled with fluid contents.

Preferably, the method includes the step of removing a plug from a mounting member of the barrel prior to removably mounting the replaceable needle assembly to the barrel.

In one embodiment, the method includes the step of screw-threadedly mounting a needle mount of the replaceable needle assembly to a mounting member of the barrel.

In a seventh aspect, the invention provides a method of making a pre-filled syringe including the steps of coupling a plunger and a seal in a syringe barrel, wherein the syringe barrel comprises fluid contents, a plug member mounted thereto or a replaceable needle assembly of the first aspect mounted thereto.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION

Figure 1:
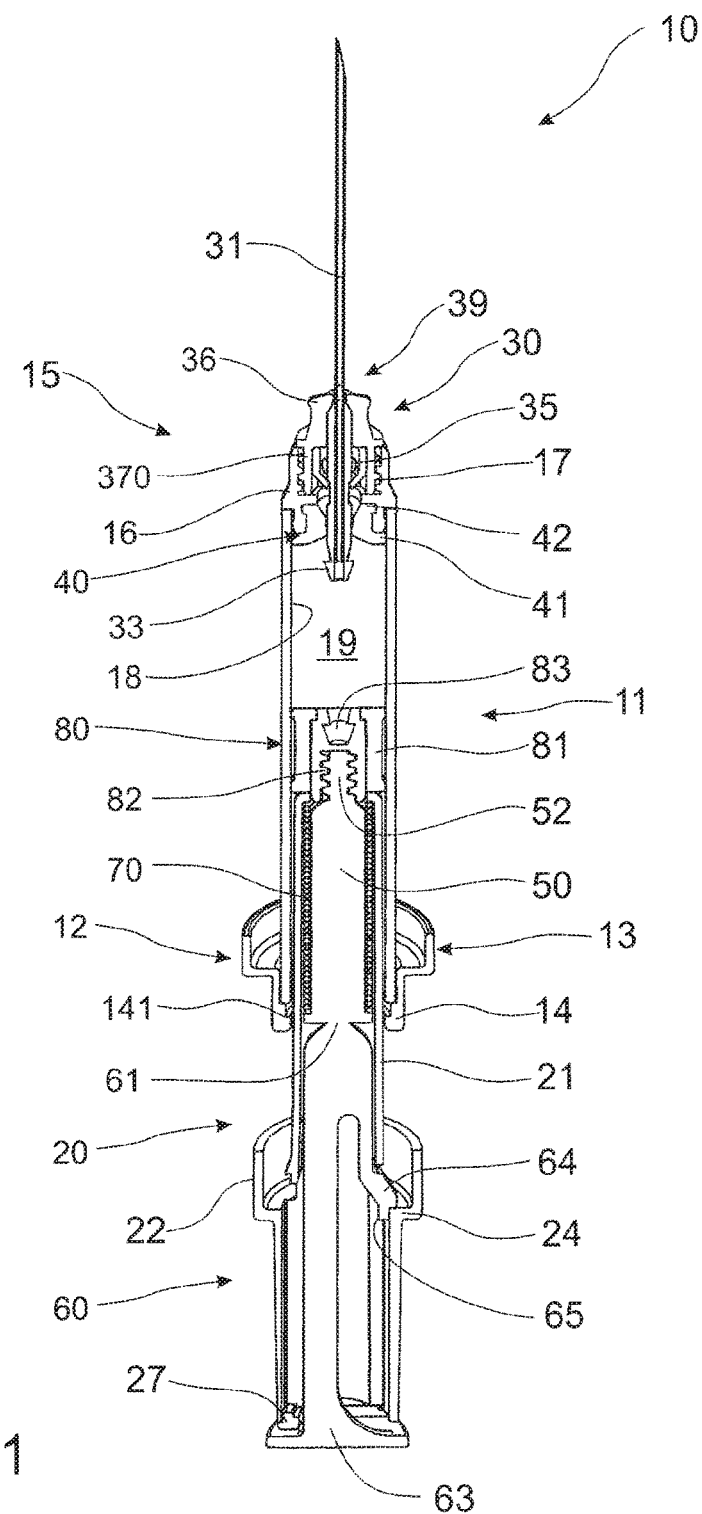
FIG. 1 is a sectional view of an embodiment of a retractable syringe.

Referring to FIG. 1, an embodiment of syringe 10 comprises barrel 11 and plunger 20 which is slidably, axially moveable within barrel 11, plunger 20 having plunger member 50 and plunger housing 21. Replaceable needle assembly 30 comprises retractable needle 39 that comprises cannula 31 and needle body 32 comprising plunger-engaging foot 33, needle mount 36 having screw threaded portion 370 and needle retainer 35. Seal 80 is mounted to projection 52 of plunger member 50. Barrel 11 comprises plunger end 12 at which is located collar 13 comprising release ring 14 having rim 141. Barrel 11 also comprises needle end 15 having mounting member 16 onto which can be mounted replaceable needle assembly 30. Mounting member 16 comprises screw thread 17 and is typically glued or otherwise firmly affixed inside needle end 15 of barrel 11. Needle seal 40 is also mounted inside needle end 15 of barrel 11 behind mounting member 16 (i.e proximal to the user). Sealing base 41 of needle seal 40 seals against inside wall 18 of barrel while body 42 is coupled to mounting member 16.

Figure 2:
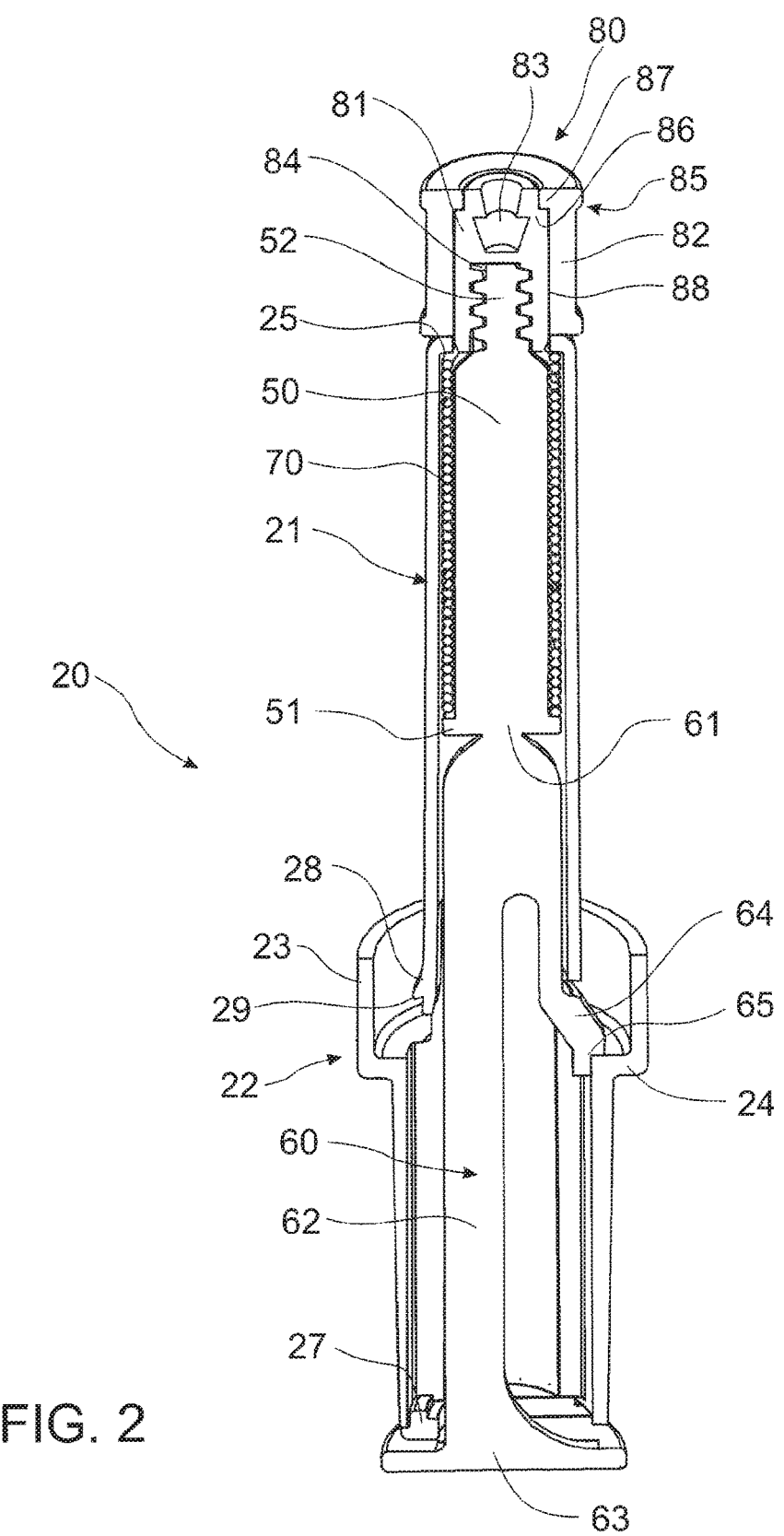
FIG. 2 is a sectional view of an embodiment of a plunger.

Referring now to FIG. 2, plunger 20 comprises plunger housing 21 with skirt 22 having flange 23 comprising inner circumferential ledge 24. Skirt 22 also comprises step 27 at an end of skirt 22 proximal to a user. Plunger housing 21 further comprises arm 28 having shoulder 29. Control rod 60 is releasably connected to plunger member 50 by way of frangible connection 61. Control rod further comprises shaft 62, button 63 which is operable by a user and trigger 64 which comprises notch 65. In this embodiment, the biasing means is spring 70. Before retraction, trigger 64 of control rod 60 engages flange 23 of plunger housing 21 by way of notch 65 releasably engaging inner circumferential ledge 24. This retains spring 70 in an initially compressed state, compressed between inner shoulder 25 of plunger housing and annular base 51 of plunger member 50. In this context, "initially compressed" means that spring 70 is in a compressed (i.e energized) state before use of the retractable syringe.

Plunger member 50 further comprises projection 52, which in this embodiment is screw threaded, which is coupled to plunger seal 80. Plunger seal 80 comprises inner member 81 and outer member 82 that are releasably coupled. Stop 85 is formed between shoulder 86 of inner member 81 and ledge 87 of outer member 82 to minimize or prevent unwanted forward travel of inner member 81 relative to outer member 82 (i.e towards needle end 15 of barrel 11), particularly when plunger 20 is initially inserted into barrel 10. Stop 85 selectively allows axial movement of inner member 81 relative to outer member 82 towards the user during retraction, as will be described in more detail hereinafter. Inner member 81 further comprises complementary mating portion 83 for receiving and engaging foot 33 of needle body 32 and plunger-engaging recess 84 that is screw-threadedly mounted to projection 52 of plunger member 50. Outer member 82 seals against inside wall 18 of barrel to prevent fluid leaking from fluid space 19. It is also noted that inner member 81 and outer member 82 provide a fluid-tight seal at internal interface 88. Although not shown, complementary annular ribs and grooves could be added to inner member 81 and outer member 82, or vice versa, to facilitate the fluid-tight seal.

Figure 3:
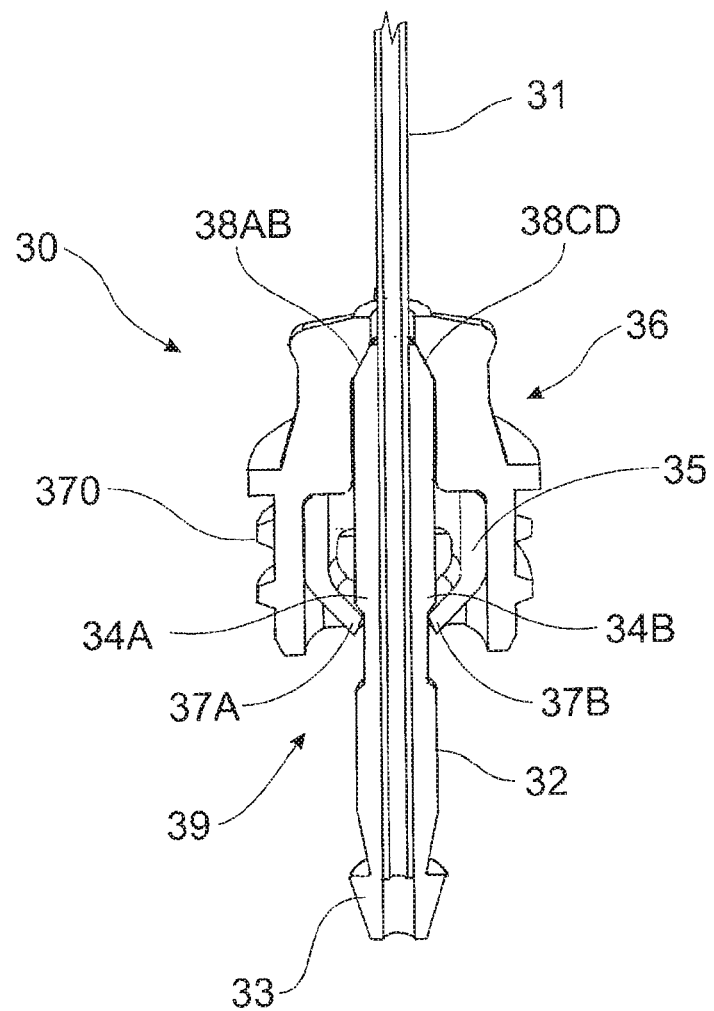
FIG. 3 is a sectional view of an embodiment of a replaceable needle assembly.

As shown in FIG. 3, replaceable needle assembly 30 comprises retractable needle 39 comprising cannula 31, needle body 32 that comprises plunger-engaging foot 33 and shoulders 34A, 34B, needle retainer 35 and needle mount 36 having screw threaded "male" portion 370. Needle retainer 35 also comprises fingers 37A, B that respectively bear against shoulders 34A, 34B of needle body 32 which retain retractable needle 39 in needle assembly 30 and prevent inadvertent retraction of retractable needle 39. This retaining function can withstand up to a 6N force, but nevertheless allow spring-driven retraction of retractable needle 39, as will be described in more detail hereinafter. An advantage of this arrangement is that no other structure (e.g. an ejector member) is required to release retractable needle 39 from fingers 37A, 37B. Complementary angled faces 38A, B, C and D also assist preventing inadvertent ejection of retractable needle, if for example subjected to a "needle pull" force 39 from needle assembly 30.

Figures 4A, 4B:
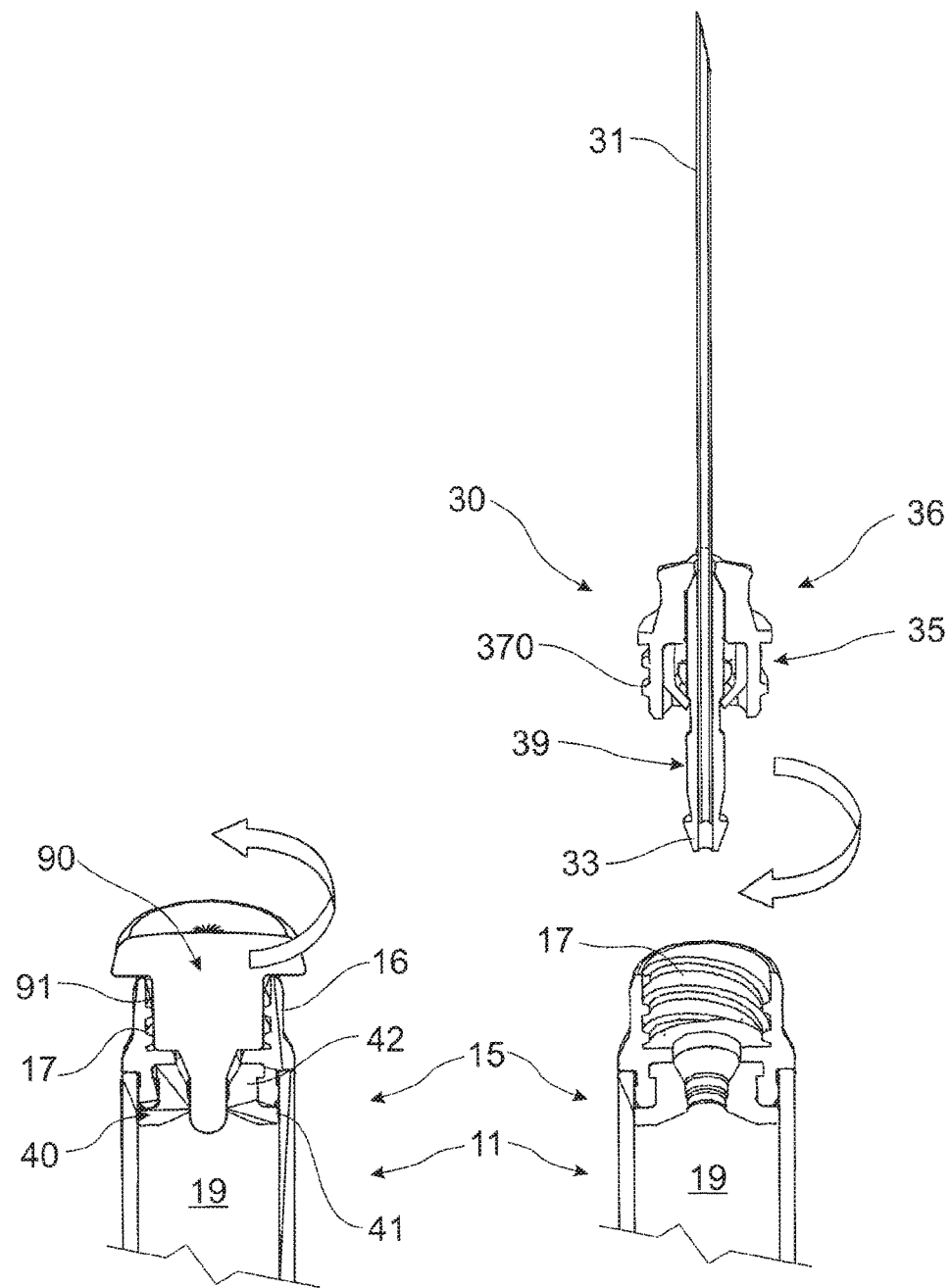
FIG. 4A is a sectional view of an embodiment of a barrel prior to removal of a plug and FIG. 4B is a sectional view showing mounting of a replaceable needle assembly to a barrel mounting member.

Referring now to FIGS. 4A and 4B, syringe 10 is typically provided prefilled with fluid contents, such as a vaccine, although without limitation thereto. As is evident in FIG. 4A, prior to use, plug 90 comprising screw-threaded portion 91 has been fitted into complementary screw-thread 17 of mounting member 16 at needle end 15 of barrel 11 to thereby seal barrel 11. Plug 90 is then unscrewed as indicated by the arrow and removed by the user so that replaceable needle assembly 30 can be mounted by way of screw thread 35 in needle mount 36 engaging complementary screw thread 17 in mounting member 16. Replaceable needle assembly 30 may be provided with a removable cover (not shown) for cannula 31 and also a screw-threaded cover (not shown) mountable to screw thread 35 of needle mount 36. Once these covers are removed and the needle assembly mounted to barrel 11, syringe 10 is ready for use. It will be appreciated that the replaceable needle assembly 30 allows a user to replace a needle that becomes bent or burred. Furthermore, a user may select an appropriate size or gauge needle for delivery.

Figure 5:
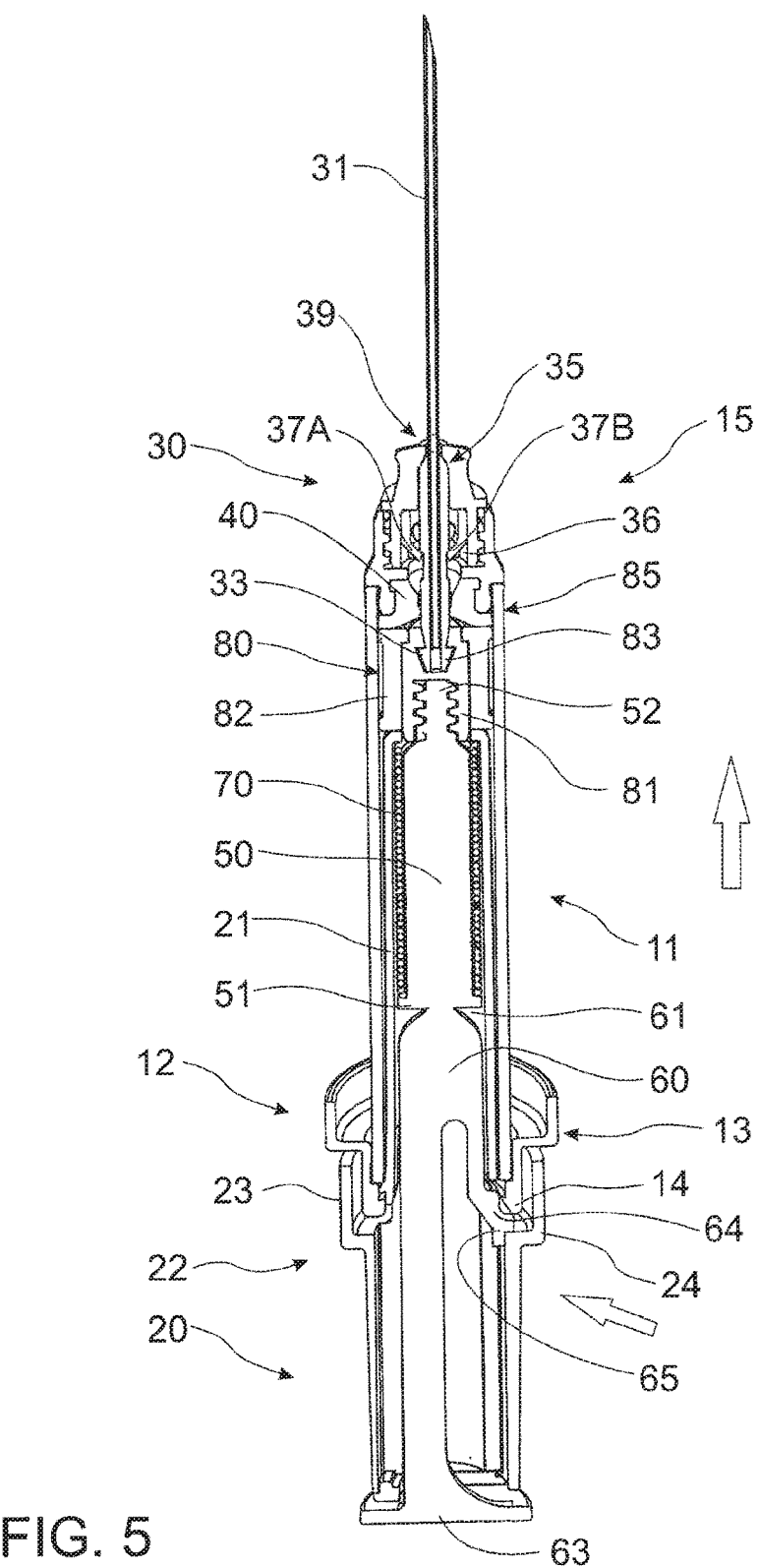
FIG. 5 is a sectional view of a plunger engaging a needle assembly prior to needle retraction.

Referring to FIG. 5, in use plunger 20 is moved axially in the direction of the solid arrow toward needle end 15 of barrel 11 to deliver fluid contents of syringe 10. At or near the end of plunger 20 depression, complementary mating portion 83 of seal inner 81 receives and snap-lock engages foot 33 of needle body 32. This effectively couples retractable needle 39 to plunger member 50, as shown in FIG. 5. It will also be appreciated that while this embodiment describes male-female engagement between foot 33 and complementary mating portion 83, the reverse arrangement is also contemplated.

The sequence of events that occur to facilitate controlled retraction of retractable needle 39 is as follows.

Continued movement of plunger 20 in the direction of the solid arrow in FIG. 5 is allowed by seal 80 and needle seal 40, which are formed of a compressible material and allow continued movement of plunger housing 21 toward needle end 15 of barrel 11 until release ring 14 bears against arm 64 of control rod 60, thereby moving trigger 64 radially inwardly in the direction of the arrow in FIG. 5. This disengages notch 65 from inner circumferential ledge 24 which thereby triggers release of control rod 60 from plunger housing 21. This allows initially compressed spring 70 to decompress and forcibly bear against annular base 51 of plunger member 50 to thereby retract plunger member 50 and connected control rod 60. Retraction of plunger member 50 occurs with sufficient force to dislodge needle body 32 from fingers 37A, B of needle retainer 35. At this time, inner member 81 of plunger seal 80 uncouples from outer member 82, moving axially towards the user so that cannula 31 and needle body 32, which is coupled to inner sealing member 81 mounted to plunger member 50, retracts in the direction of the arrow in FIG. 6 (inside plunger housing 21 which remains stationary relative to barrel 11).

Figure 7:
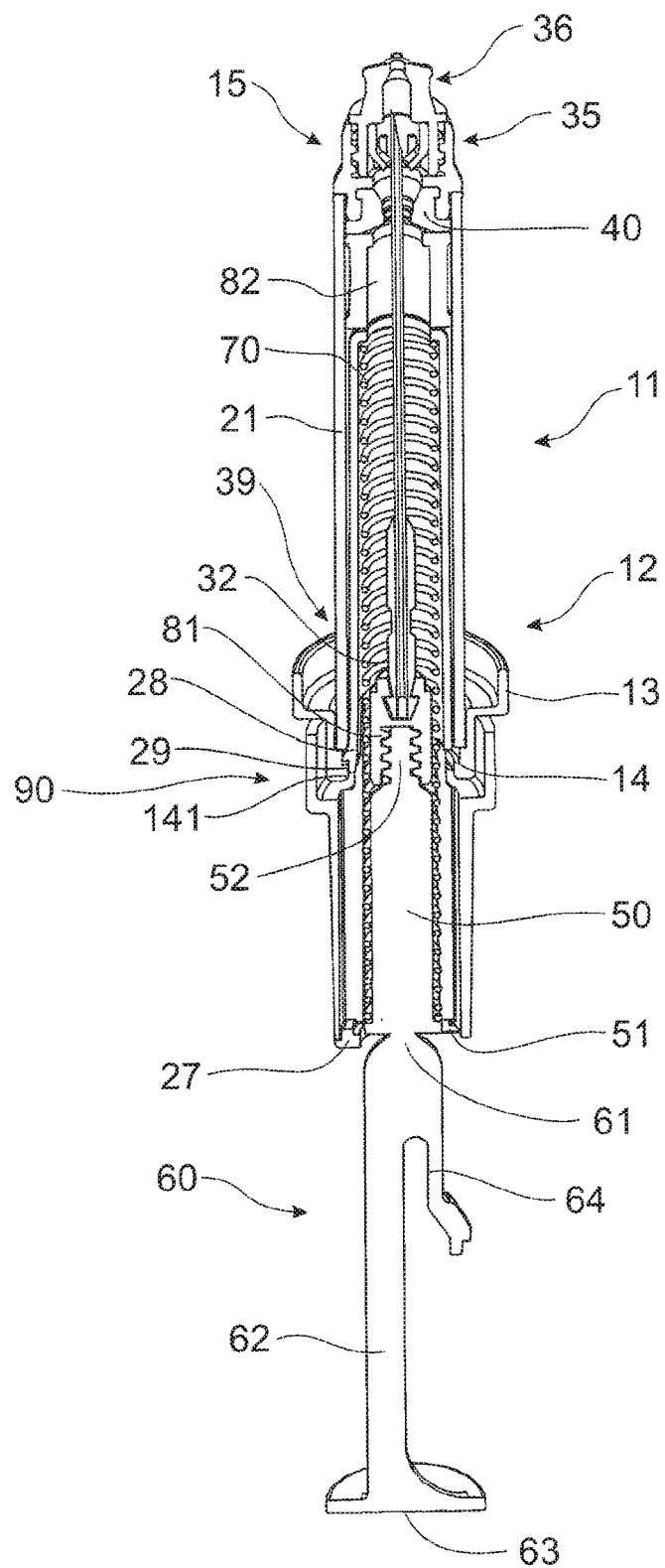
FIG. 7 is a sectional view showing an embodiment of a retractable syringe after retraction of a retractable needle.

Accordingly, control rod 60 retracts, the rate of which retraction is controlled by a user relaxing pressure (such as by way of thumb pressure) against control button 63. As shown in FIG. 7, retraction is complete when base 51 of first plunger member 50 abuts step 27 in plunger housing 21 which is stationary during retraction of plunger member 50 and control rod 60. Needle seal 40, needle mount 36 and needle retainer 35 also remain stationary at needle end 15 of barrel 11.

Figure 6:
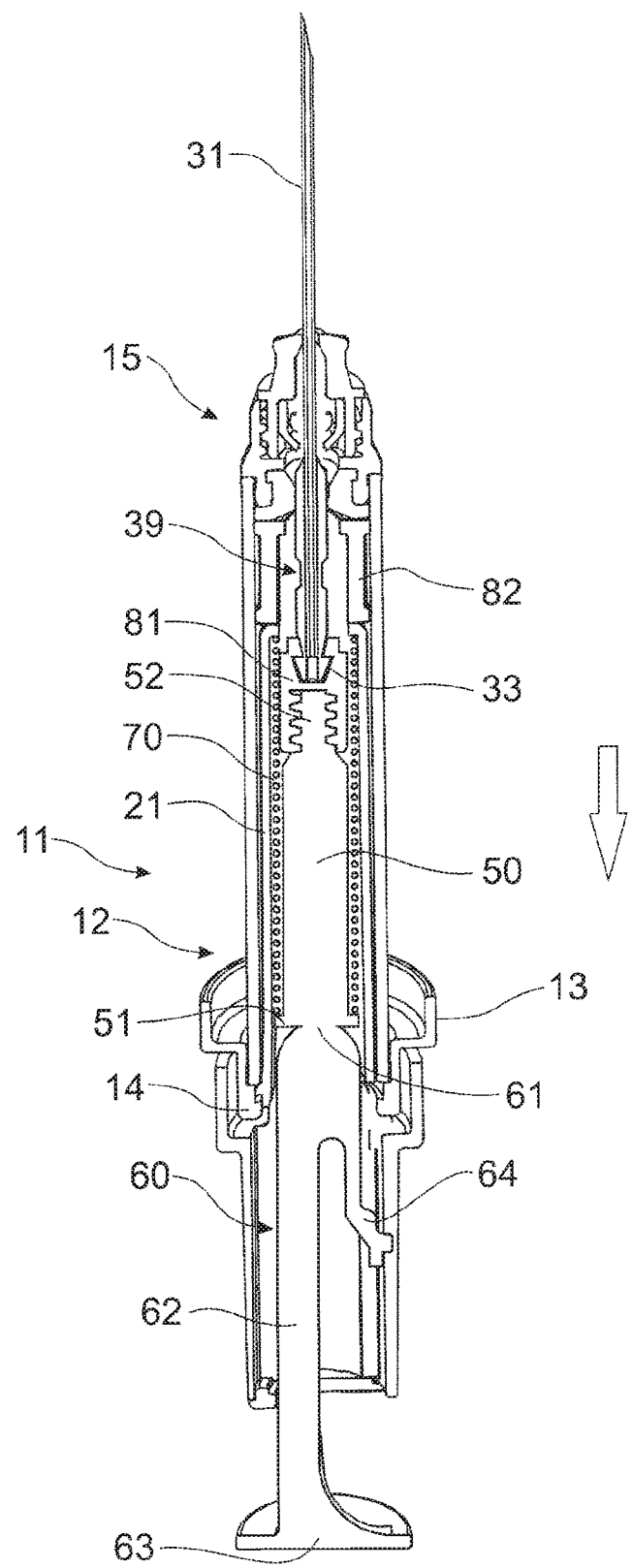
FIG. 6 is a sectional view showing spring-driven retraction of a plunger, plunger rod and retractable needle.

As shown in FIGS. 6 and 7, at the end of plunger 20 depression to complete injection of fluid contents of syringe 10, lock 90 is formed between lock elements in the form of shoulder 29 of arm 28 of plunger housing 21 locked onto rim 141 inside release ring 14 of collar 13 at plunger end 12 of barrel 11, to thereby prevent withdrawal of plunger housing 21 from barrel 11. This also facilitates ease of removal of control rod 60, which can be manually removed from syringe 10 by breaking control rod 60 away from plunger member 50 at frangible connection 61. Control rod 60 may then be discarded as "clean" waste, leaving syringe 10 with plunger housing 21 and plunger member 50 remaining inside barrel 11 for a more compact medical waste disposal.

In light of the foregoing it will be appreciated that the present invention provides a relatively simple, robust and inexpensive syringe that is automatically disabled with little or no assistance from the user to thereby prevent, or at least minimize the likelihood of, re-use of the syringe or needlestick injury to the user.

Furthermore, the replaceable needle assembly allows a user to select a needle of appropriate size of gauge or needle length and/or to replace a needle that becomes bent or burred. Another advantage of the retractable syringe described herein is that it can accommodate and fully encapsulate on retraction, needles of varying length up to 1.5 inches (~3.8 cm) in length, thereby providing great flexibility to the user.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A replaceable needle assembly for a retractable syringe comprising a plunger and a barrel that comprises a mounting member, the replaceable needle assembly comprising:
   a needle mount that is removably mountable to the mounting member of the barrel;
   a retractable needle including a cannula and a needle body that is removably mountable to the needle mount, the needle body being engageable by the plunger to facilitate retraction of the retractable needle from the needle mount; and
   a needle retainer that releasably engages the needle body of the retractable needle to prevent inadvertent retraction of the retractable needle, the retractable needle extending both proximally and distally from the needle mount and needle retainer prior to retraction;
   wherein the needle retainer permits retraction of the retractable needle solely in response to a retraction force applied by the plunger when engaged with the needle body.

2. The replaceable needle assembly of claim 1, wherein the needle retainer comprises a plurality of fingers that releasably engage the retractable needle to thereby prevent inadvertent retraction of the retractable needle.

3. The replaceable needle assembly of claim 1, wherein the needle mount comprises a screw threaded portion.

4. The replaceable needle assembly of claim 1, wherein the needle mount and the needle body comprise complementary angled faces configured to prevent inadvertent ejection of the retractable needle.

5. The replaceable needle assembly of claim 1, wherein the needle body includes at least one shoulder, the needle retainer bearing against the at least one shoulder to retain the retractable needle.

6. The replaceable needle assembly of claim 5, wherein the needle body includes two shoulders and the needle retainer includes at least two fingers bearing against at least one of the shoulders to retain the retractable needle.

7. The replaceable needle assembly of claim 6, wherein the at least two fingers bearing against the at least one shoulder retains the retractable needle with an application of a retraction force up to 6N.

8. A retractable syringe comprising:
a barrel having a mounting member;
a plunger comprising: a biasing means; a plunger member releasably connected to a control rod; a plunger housing; and a plunger seal mounted to the plunger member wherein the plunger member, control rod and plunger housing co-operate to maintain the biasing means in an initially energized state prior to retraction; and
a replaceable needle assembly mounted to the barrel wherein the needle assembly comprises: a needle mount that is removably mountable to the mounting member of the barrel; a retractable needle including a cannula and a needle body that is removably mountable to the needle mount, the needle body being engageable by the plunger to facilitate retraction of the retractable needle from the needle mount; and a needle retainer that releasably engages the needle body of the retractable needle to prevent inadvertent retraction of the retractable needle, the retractable needle extending both proximally and distally from the needle mount and needle retainer prior to retraction;
wherein the needle retainer permits retraction of the retractable needle solely in response to a retraction force applied by the plunger when engaged with the needle body, and the retractable needle and the control rod retract relative to the plunger housing as the biasing means releases energy at a rate controlled by a user acting upon the control rod.

9. The retractable syringe of claim 8, wherein the plunger seal of the plunger comprises a needle-engaging portion.

10. The retractable syringe of claim 9, wherein the needle-engaging portion is for engaging a foot of a needle body of a retractable needle.

11. The retractable syringe of claim 8, arranged so that at the end of depression of the plunger to deliver fluid contents of the retractable syringe , the control rod is disengageable from the plunger housing to facilitate a release of energy from the biasing means to thereby retract the control rod and the plunger member with the needle coupled thereto.

12. The retractable syringe of claim 8, wherein the barrel further comprises a collar.

13. The retractable syringe of claim 8, further comprising a lock formed between respective lock elements of the plunger housing and the collar of the barrel, which lock prevents or hinders removal of the plunger housing from the retractable syringe after retraction of the retractable needle.

14. The retractable syringe of claim 8, which is a prefilled retractable syringe.

15. The retractable syringe of claim 8, wherein the biasing means is a spring.

16. The retractable syringe of claim 8, further comprising a needle seal.

17. The retractable syringe of claim 8, wherein the mounting member includes a screw thread.

18. A retractable syringe kit comprising:
a barrel prefilled with fluid contents and having a mounting member;
a plunger, the plunger comprising: a biasing means; a plunger member releasably connected to a control rod; a plunger housing; and a plunger seal mounted to the plunger member; wherein the plunger member, control rod and plunger housing co-operate to maintain the biasing means in an initially energized state prior to retraction; and
a plurality of replaceable needle assemblies each comprising: a needle mount that is removably mountable to the mounting member of the barrel; a retractable needle including a cannula and a needle body that is removably mountable to the needle mount, the needle body being engageable by the plunger to facilitate retraction of the retractable needle from the needle mount; and a needle retainer that releasably engages the needle body of the retractable needle to prevent inadvertent retraction of the retractable needle, the retractable needle extending both proximally and distally from the needle mount and needle retainer prior to retraction; wherein the needle retainer permits retraction of the retractable needle solely in response to a retraction force applied by the plunger when engaged with the needle body.

19. The retractable syringe kit of claim 18, wherein the plurality of needle assemblies respectively comprise a 0.5 inch needle, a 1.0 inch needle and a 1.5 inch needle.

20. The retractable syringe kit of claim 18, which comprises a plug removably mounted to the mounting member of the barrel.

* * * * *